(12) United States Patent
Monti

(10) Patent No.: US 10,322,138 B2
(45) Date of Patent: Jun. 18, 2019

(54) TREATMENT OF DEPRESSIVE DISORDERS

(71) Applicant: Pherin Pharmaceuticals, Inc., Los Altos, CA (US)

(72) Inventor: Louis Monti, Mountain View, CA (US)

(73) Assignee: PHERIN PHARMACEUTICALS, INC., Los Altos, CA (US)

( * ) Notice: Subject to any disclaimer, the term of this patent is extended or adjusted under 35 U.S.C. 154(b) by 0 days.

(21) Appl. No.: 14/134,906

(22) Filed: Dec. 19, 2013

(65) Prior Publication Data

US 2014/0187524 A1    Jul. 3, 2014

Related U.S. Application Data

(60) Provisional application No. 61/747,167, filed on Dec. 28, 2012.

(51) Int. Cl.
| | |
|---|---|
| *A61K 9/00* | (2006.01) |
| *A61K 9/08* | (2006.01) |
| *A61K 31/57* | (2006.01) |
| *A61K 45/06* | (2006.01) |
| *A61K 47/10* | (2017.01) |

(52) U.S. Cl.
CPC ............ *A61K 31/57* (2013.01); *A61K 9/0043* (2013.01); *A61K 9/08* (2013.01); *A61K 45/06* (2013.01); *A61K 47/10* (2013.01)

(58) Field of Classification Search
USPC ....................................................... 514/177
See application file for complete search history.

(56) References Cited

U.S. PATENT DOCUMENTS

| | | | |
|---|---|---|---|
| 5,303,703 | A | 4/1994 | Monti-Bloch |
| 5,563,131 | A | 10/1996 | Berliner et al. |
| 5,994,333 | A | 11/1999 | Jennings-White et al. |
| 6,057,439 | A | 5/2000 | Jennings-White et al. |
| 6,066,627 | A | 5/2000 | Jennings-White et al. |
| 6,117,860 | A | 9/2000 | Jennings-White et al. |
| 6,331,534 | B1 | 12/2001 | Berliner et al. |
| 2002/0123138 | A1 | 9/2002 | Zhang et al. |
| 2003/0045514 | A1 | 3/2003 | Monti et al. |

FOREIGN PATENT DOCUMENTS

WO     94/28904 A1     12/1994

OTHER PUBLICATIONS

Andrew (Dimensionality and the catergory of major depressive episode, Internation Journal of Method in Psychiatric Research, 16(S1), 2007 pp. S41-S51).*
Goldstein (Duloxetine in the treatmentof major depressive disorder: a double-blind clinical trial, J Clin Psychiatry, 2002, 63(3) pp. 225-231, abstract only).*
Remington's, The Science and Practice of Pharmacy, 21st Edition, 2001, pp. 221, 291, 747).*
Remington's, The Science and Practice of Pharmacy, 21st Edition, 2001, p. 261.*
Grosser et al., "Behavioral and electrophysiological effects of androstadienone, a human pheromone", Psychoneuroendocrinology, 2000, 25:289-299.
Krubiner et al., "The Synthesis of 17-Deoxy-17-α and -17β 20-pregnynes and 20-pregnenes", J. Org. Chem., 1969, 34(11):3502-3505.
Manber et al., "Cognitive Behavioral Therapy for Insomnia Enhances Depression Outcome in Patients with Comorbid Major Depressive Disorder and Insomnia", Sleep, 2008, 31(4):489-495.
Monti-Bloch et al., "Effect of putative pheromones on the electrical activity of the human vomeronasal organ and olfactory epithelium", J. Steroid Biochem. Mol. Biol., 1991, 39(4B):573-582.
Monti-Bloch et al., "The Human Vomeronasal System: A Review", Ann. N.Y. Acad. Sci., 1998, 855:373-389.
Stensaas et al., "Ultrastructure of the human vomeronasal organ", J. Steroid Biochem. Mol. Biol., 1991, 39(4B):553-560.
Smolensky et al., "Diurnal and twenty-four hour patterning of human diseases: acute and chronic common and uncommon medical conditions", Sleep Med. Rev., 21, 12-22 (2015).

* cited by examiner

*Primary Examiner* — Kathrien A Cruz
(74) *Attorney, Agent, or Firm* — Hamilton Desanctis & Cha, LLP; Sam L. Nguyen

(57) ABSTRACT

Pregn-4-en-20-yn-3β-one is useful in the treatment of depressive disorders by nasal administration.

21 Claims, No Drawings

TREATMENT OF DEPRESSIVE DISORDERS

CROSS-REFERENCE TO RELATED APPLICATIONS

This application claims the benefit under 35 USC 119(e) of U.S. Provisional Application No. 61/747,167, filed 28 Dec. 2012, "Treatment of depressive disorders", which is incorporated into this application by reference.

BACKGROUND OF THE INVENTION

Field of the Invention

This invention relates to the treatment of depressive disorders.

Description of the Related Art

Depression

Depression is a common mental disorder and refers to a mental state of low (depressed) mood and aversion to activity. Symptoms associated with depression include persistent anxious or sad feelings, feelings of helplessness, hopelessness, pessimism, and/or worthlessness, low energy, restlessness, irritability, fatigue, loss of interest in pleasurable activities or hobbies, excessive sleeping or insomnia, overeating or appetite loss, thoughts of suicide, and suicide attempts. The presence, number, severity, frequency, and duration of these symptoms may vary from individual to individual and from time to time for a given individual.

Psychiatrists classify mental disorders, such as depression, using the classifications such as those in the DSM-IV-TR (Diagnostic and Statistical Manual of Mental Disorders, Fourth Edition, Text Revision, American Psychiatric Association, Washington DC, 2000). The most common types of depression are Major Depressive Disorder (MDD), classified in the DSM-IV-TR under code 296.3x (see DSM-IV-TR at pages 349-356 for a description of Major Depressive Episode and pages 369-376 for MDD) and Dysthymic Disorder (DD), classified in the DSM-IV-TR under code 300.4 (see DSM-IV-TR at pages 345-348 and 376-381). Diagnostic criteria for MDD are, in summary, the presence of at least one Major Depressive Episode (i.e. the presence of five or more symptoms nearly every day from (1) depressed mood—may be irritable mood in children or adolescents, (2) loss of interest or pleasure in everyday activities, (3) significant weight loss or gain, or decrease or increase in appetite, (4) insomnia or hypersomnia, (5) psychomotor agitation or retardation, (6) fatigue or loss of energy, (7) feelings of worthlessness or excessive or inappropriate guilt, (8) diminished ability to think or concentrate, and (9) recurrent thoughts of death, recurrent suicidal ideation, or attempt at suicide or specific plan for suicide; including at least one of (1) and (2) present during the same 2-week period, representing a change from previous functioning; the symptoms causing clinically significant distress or impairment, and not due to the effects of a substance, medical condition, or bereavement) not better accounted for by other conditions, and lack of manic, mixed, or hypomanic episodes. Diagnostic criteria for DD are, in summary, (1) a depressed mood for most of the day for the majority of days over at least 2 years—over at least 1 year in children or adolescents, and may be irritable mood; (2) the presence, while depressed, of symptoms such as sleep disturbances, fatigue, and feelings of hopelessness; (3) no continuous period of more than 2 months during the 2 years—1 year for children or adolescents—without the symptoms in (1) and (2); and no major depressive episode present in the first 2 years—1 year for children or adolescents—of the disturbance, so that the disorder is not better accounted for by MDD. As the DSM-IV-TR notes (page 374), MDD and DD are differentiated based on severity, chronicity, and persistence, and "the differential diagnosis between them is made particularly difficult by the fact that the two disorders share similar symptoms . . . ". Other depression conditions may develop under special circumstances, and the DSM-IV-TR includes "specifiers" such as postpartum onset (pages 422-423), and seasonal pattern (pages 425-427) as potentially applicable to MDD—referring to the conditions commonly called postpartum depression and seasonal affective disorder. The DSM-IV-TR includes under Depressive Disorder Not Otherwise Specified (code 311, pages 381-382) minor depressive disorder (episodes of at least 2 weeks of depressive symptoms but with fewer than the five items required for MDD), and recurrent brief depressive disorder (depressive episodes lasting for from 2 days to 2 weeks at least once/month for 12 months and not associated with the menstrual cycle). The DSM-IV-TR also includes under Mood Disorder Due to General Medical Condition With Depressive Features or Mood Disorder Due to General Medical Condition With Major Depressive-Like Episode (code 293.83, pages 401-406) a predominantly depressed mood that is the physiological consequence of a general medical condition; and under Adjustment Disorder With Depressed Mood (code 309.0, pages 679-683) a depressed mood in response to a stressor, which may include a medical condition. Because depressed mood is frequently associated with chronic medical conditions such as cancer and chronically painful conditions, it is convenient to consider these last three conditions together when the Adjustment Disorder With Depressed Mood is associated with a medical condition as "depressive disorders associated with a medical condition".

The Pharmacological Treatment of Depression

A number of antidepressant medications are available for use in treating depression. They are generally characterized by their effect on naturally occurring brain chemicals:

(1) selective serotonin reuptake inhibitors (SSRIs) include citalopram (CELEXA), escitalopram (LEXAPRO), fluoxetine (PROZAC), paroxetine (PAXIL), and sertraline (ZOLOFT). These are the most common initial treatment for depression because they are safer and generally cause fewer bothersome side effects than do other types of antidepressants. The most common side effects include decreased sexual desire and delayed orgasm. Other side effects, which can include digestive problems, jitteriness, restlessness, headache, and insomnia, may decrease over time;

(2) serotonin/norepinephrine reuptake inhibitors (SNRIs) include desvenlafaxine (PRISTIQ), duloxetine (CYMBALTA), and venlafaxine (EFFEXOR XR). The side effects are similar to those caused by SSRIs and they can cause increased sweating, dry mouth, fast heart rate, and constipation;

(3) norepinephrine/dopamine reuptake inhibitors (NDRIs) include bupropion (WELLBUTRIN). Bupropion is one of the few antidepressants that does not cause sexual side effects, though at high doses it may increase the risk of seizures;

(4) atypical antidepressants include mirtazapine (REMERON) and trazodone (OLEPTRO). These antidepressants are sedating and are usually taken in the evening. The newest atypical depressant, vilazodone (VIIBRYD), has a low risk of sexual side effects but its most common side effects are diarrhea, nausea, vomiting, and insomnia;

(5) tricyclic antidepressants include desipramine (NORPRAMIN), doxepin (SILENOR), imipramine (TOFRANIL), maprotiline, protryptaline (VIVACTIL), and trimipramine (SURMONTIL). These have been used for many years and are generally as effective as newer medications—they are generally SNRIs in effect but with an antihistaminic and anticholinergic side effect—but they are generally used only when SSRI/SNRI treatment is ineffective because they tend to have more numerous and more severe side effects which can include dry mouth, blurred vision, constipation, urinary retention, bradycardia, confusion, and weight gain;

(6) monoamine oxidase inhibitors (MAOIs) include phenelzine (NARDIL) and tranylcypromine (PARNATE). These are usually prescribed only as a last resort when other medications have not worked, because they can have serious side effects. They require a strict diet because of dangerous and potentially deadly interactions with tyramine-containing foods, for example certain cheeses, pickles, and wines, and some medications including decongestants, and cannot be combined with SSRIs.

All of these and similar antidepressant medications ("conventional antidepressant therapy") are associated with side effects of varying degrees of significance; and most take several weeks, typically three or more weeks and up to eight weeks, to take full effect and for side effects to ease.

Association of Depression with Sleep Disorders

As noted above, one of the criteria that may be used to diagnose a Major Depressive Episode is insomnia or hypersomnia; and both the scientific and popular literature note a high incidence of sleep disturbances, particularly insomnia, in individuals suffering from depression. Unfortunately, one of the common side effects of the SSRIs and SNRIs, the most common pharmacological treatments for depression, is insomnia. Manber et al., "Cognitive Behavioral Therapy for Insomnia Enhances Depression Outcome in Patients with Comorbid Major Depressive Disorder and Insomnia", *Sleep*, 2008, 31(4):489-495, report that insomnia symptoms hinder response to antidepressant treatment, and that continued insomnia following the acute phase of antidepressant therapy poses a significant risk for relapse. In a pilot study with 30 individuals diagnosed with MDD and insomnia, they found that treatment for the depression with escitalopram plus treatment for the insomnia with cognitive behavioral therapy nearly doubled the rate of rate of remission of the depression (61.5%) over treatment with escitalopram plus a control quasi-desensitization therapy (33.3%), while remission of insomnia was more than 6-fold higher (50.0% compared with 7.7%).

Nasal Chemosensory Receptors, the Vomeronasal Organ, and Pherines

Nasal chemosensory receptors, including the vomeronasal organ ("VNO"; also known as "Jacobson's organ", a bilateral chemosensory organ found in most vertebrates including humans) are found in the mucosal lining of the nasal septum and the dorsal nasal recess, and have been associated with pheromone reception in most species (see generally Muller-Schwarze and Silverstein, "Chemical Signals", Plenum Press, New York (1980); Monti-Bloch et al., "Effect of putative pheromones on the electrical activity of the human vomeronasal organ and olfactory epithelium", *J. Steroid Biochem. Mol. Biol.*, 1991, 39(4):573-582; Monti-Bloch et al., "The Human Vomeronasal System: A Review", *Ann. N.Y. Acad. Sci.*, 1998, 855:373-389). The axons of the neuroepithelia of the nasal chemosensory receptors, including the VNO, have direct input to the hypothalamus and limbic amygdala of the brain, while the distal processes (microvilli) may serve as chemosensory receptors (Stensaas et al., "Ultrastructure of the human vomeronasal organ", *J. Steroid Biochem. Mol. Biol.*, 1991, 39(4):553-560).

Human pheromones delivered to the nasal septal area bind to local chemosensory receptors and trigger nerve signals that reach the brain inducing physiological and behavioral changes (Grosser et al., "Behavioral and electrophysiological effects of androstadienone, a human pheromone", *Psychoneuroendocrinology*, 2000, 25:289-299). Synthetic analogs of human pheromones called pherines (substances that bind to nasal chemosensory receptors, including receptors in the VNO) can induce robust physiological, pharmacological and behavioral changes when delivered airborne to these receptors via the nasal passages. This information is supported by several studies in human volunteers using functional magnetic resonance imaging and positron emission tomography, showing that pherines selectively activate the brain areas (hypothalamus, limbic system, cingulate gyrus, anterior thalamus and prefrontal cortex) where their physiological, pharmacological and behavioral effects are integrated. Studies with several pherines have shown that, because the compounds act directly on nasal chemosensory receptors which are directly connected to the brain, administration of the compounds causes an effect on physiological markers (e.g. autonomic nervous system responses and EEG) within seconds to less than a minute, and an effect on endocrine and neurotransmitter metabolite markers within about 10-15 minutes.

Monti et al., US Patent Application Publication No. 2003/0045514, "17-methyleneandrostan-3α-ol analogs as CRH inhibitors" discloses certain 17-methyleneandrostan-3α-ol analogs as inhibitors of corticotropin releasing hormone, potentially useful as antidepressants by vomeronasal administration.

Pregn-4-en-20-yn-3-one

Pregn-4-en-20-yn-3-one and its synthesis are described in Krubiner et al., "The Synthesis of 17-Deoxy-17-α and -17β20-pregnynes and -20-pregnenes", *J. Org. Chem.*, 1969, 34(11):3502-3505. Berliner et al., U.S. Pat. No. 5,563,131, "Pregnane steroids as neurochemical initiators of change in human hypothalamic function and related pharmaceutical compositions and methods", describes the use of a number of pregnane steroids as compounds capable of altering hypothalamic or autonomic function by administration to the vomeronasal organ of an individual. Pregn-4-en-20-yn-3-one is disclosed in the patent, where it is compound A1/P5 in the chart of pregnanes (bottom left of column 18, described as "known") and is referred to as pregn-4-en-3-on-20-yne (column 61, line 26, Example 15, disclosing it as a starting material for pregn-4-en-20-yn-3β-ol). The patent generically claims pharmaceutical compositions containing the compound and methods of altering hypothalamic or autonomic function with it by vomeronasal administration, although no data are given for the compound. A continuation-in-part, Jennings-White et al., U.S. Pat. No. 5,994,333, "Pregnane and cholane steroids as neurochemical initiators of change in hypothalamic function and related pharmaceutical compositions and methods", has the same disclosure. Some later patents, such as Jennings-White et al., U.S. Pat. No. 6,057,439, "Steroids as neurochemical stimulators of the VNO to alleviate symptoms of PMS and anxiety", Jennings-White et al., U.S. Pat. No. 6,066,627, "Steroids as neurochemical initiators of change in human blood levels of LH", Jennings-White et al., U.S. Pat. No. 6,117,860, "Steroids as neurochemical stimulators of the VNO to treat paroxistic tachycardia", and Berliner et al., U.S. Pat. No. 6,331,534, "Steroids as neurochemical stimulators of the VNO to alleviate pain", have similar disclosures with regard to pregn-4-en-20-yn-3-one, while including many steroids of different classes.

The disclosures of the documents referred to in this application are incorporated into this application by reference.

SUMMARY OF THE INVENTION

In a first aspect, this invention is a method for the treatment of depressive disorders (treatment of individuals suffering from depressive disorders) by nasal administration of pregn-4-en-20-yn-3-one.

In other aspects, this invention thus includes:

pregn-4-en-20-yn-3-one for the treatment of depressive disorders by nasal administration; pharmaceutical formulations and devices containing pregn-4-en-20-yn-3-one for the treatment of depressive disorders by nasal administration; and the use of pregn-4-en-20-yn-3-one in the manufacture of medicaments for the treatment of depressive disorders by nasal administration.

Pregn-4-en-20-yn-3-one has particular utility in the treatment of depressive disorders (treatment of individuals suffering from depressive disorders); and is expected to have the following advantages over conventional antidepressants:

(1) ease of administration compared to the injectable forms of antidepressants used in the in-patient setting while retaining the ability for acute use;

(2) rapid onset of effect, because of the direct local delivery of the compound to nasal chemosensory receptors and consequent action. Current antidepressants, typically orally administered, are known to take from days to, more typically, weeks for therapeutic effectiveness to be achieved;

(3) lack of local nasal and systemic adverse effects or toxicity, because of the very low (nanogram to low microgram) doses used and the local route of administration. Most current antidepressants have a variety of side effects as described in the Description of the related art under "The pharmacological treatment of depression";

(4) lack of suppression of sexual behavior, for the same reason as (3) above. Most current antidepressants negatively affect sexual behavior (decrease in sexual drive, erectile function, and orgasm); and (5) a beneficial effect on initial insomnia (difficulty in falling asleep early in the night), thus being especially useful in the treatment of individuals suffering from depressive disorders and insomnia.

Preferred embodiments of this invention are characterized by the specification and by the features of claims 1 to 20 of this application as filed, and of corresponding pharmaceutical compositions, devices, methods, and uses of the compound.

DETAILED DESCRIPTION OF THE INVENTION

Definitions

A "depressive disorder" is a disorder selected from Major Depressive Disorder, Dysthymic Disorder, minor depressive disorder, recurrent brief depressive disorder, and a depressive disorder associated with a medical condition, as described in the Description of the related artunder "Depression".

"Nasal administration" or "intranasal administration" is administration to human nasal chemosensory receptors, including the receptors of the VNO. In a clinical setting, this may be accomplished by the use of a probe specifically designed to administer the pregn-4-en-20-yn-3-one essentially solely to the VNO (such a probe, also designed to measure the effect on vomeronasal tissue, is described in Monti-Bloch, U.S. Pat. No. 5,303,703, "Combined neuroepithelial sample delivery electrode device and methods of using same"). More usually, however, nasal administration comprises administration to the nasal passages in a manner that desirably directs the pregn-4-en-20-yn-3-one generally towards the nasal chemosensory receptors, including the receptors of the VNO.

A "therapeutically effective amount" means the amount of pregn-4-en-20-yn-3-one that, when administered to the nasal chemosensory receptors of an individual suffering from a depressive disorder, is sufficient to effect treatment for the depressive disorder, but which amount is insufficient to have a systemic effect on the depressive disorder by absorption into the circulation. "Treating" or "treatment" of a depressive disorder includes one or more of:

(1) inhibiting the occurrence of the depressive disorder, or of a symptom thereof;

(2) relieving the depressive disorder, or a symptom thereof, when it occurs, and (3) palliating the symptoms of the depressive disorder.

A "pharmaceutically acceptable excipient" means an excipient that is useful in preparing a pharmaceutical formulation that is generally safe, non-toxic, and desirable. These excipients may be solid, liquid, semisolid, or, in the case of an aerosol composition, gaseous.

"Comprising", "containing", "including", and their grammatical variants are words of inclusion and not of limitation and specify the presence of stated components, groups, steps, and the like but do not exclude the presence or addition of other components, groups, steps, and the like. Thus "comprising" does not mean "consisting of", "consisting substantially of", or "consisting only of"; and, for example, a formulation "comprising" a compound must contain that compound but also may contain other active ingredients and/or excipients.

Pregn-4-en-20-yn-3-one and Its Preparation

Pregn-4-en-20-yn-3-one is the compound of the formula

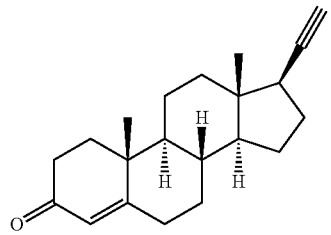

The preparation of pregn-4-en-20-yn-3-one is described in the Krubiner et al. article referred to in the Description of the related artunder "Preen-4-en-20-yn-3-one", starting from the readily commercially available steroid pregnenolone (313-hydroxy-pregn-5-en-20-one, available from a number of suppliers in various countries, such as NetQem in the US and various foreign suppliers), as illustrated in the following reaction scheme:

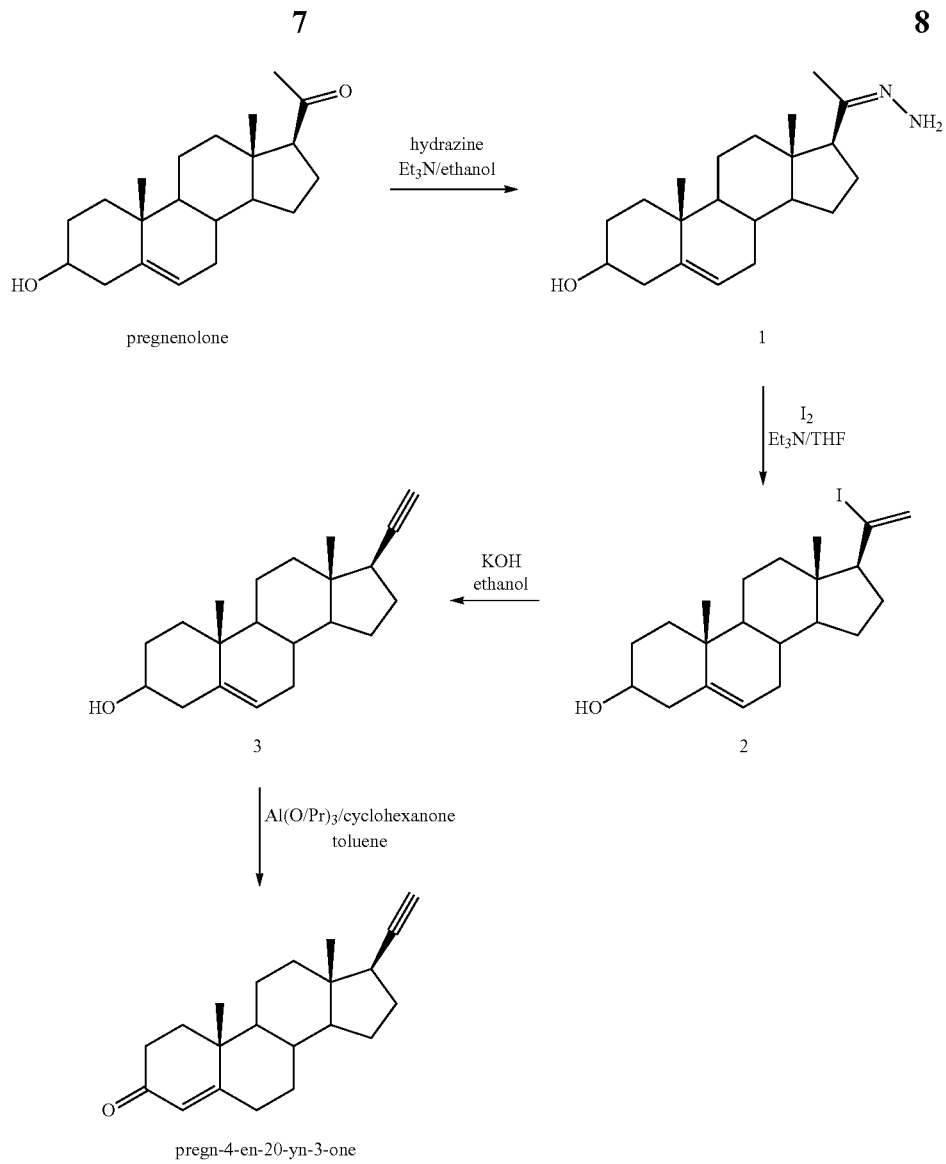

From the description of the synthesis in the Krubiner et al. article: in the first step, pregnenolone, 20 g, hydrazine hydrate, 15 mL of 85%, and trimethylamine, 75 mL, in 200 mL ethanol, are refluxed for 4 hours. The reaction mixture is poured into water, and the precipitate filtered and washed to give 1, pregnenolone hydrazone, 19.37 g.

In the second step, a solution of iodine, 36 g, in 100 mL tetrahydrofuran is added dropwise under nitrogen to a solution of 1, 19.37 g, and triethylamine, 500 mL, in 1 L anhydrous tetrahydrofuran. The iodine color disappears on addition and gas is evolved, and a precipitate of triethylamine hydriodide forms partway through the addition. At the end of the addition, the iodine color does not fade. The reaction mixture is then stirred for 1 hour, concentrated under vacuum, dissolved in dichloromethane, washed with 2N hydrochloric acid and then with 5% aqueous sodium thiosulfate, and dried. Removal of the solvent gives an oily product 2, 20-iodopregna-5,20-dien-3β-ol, that crystallizes on standing. This is crystallized from aqueous ethanol to give 2, 12.4 g.

In the third step, 2, 9.38 g, is added to a solution of potassium hydroxide, 30 g, in 350 mL ethanol, and the mixture refluxed for 4 hours, then cooled. Most of the ethanol is removed under vacuum, water is added, and the reaction mixture is acidified with 6N hydrochloric acid and extracted with ether. The ether is dried, then removed, to give 3, 3β-hydroxypregn-5-en-20-yne, as a tan solid. Two crystallizations from aqueous ethanol gives 3, 4.16 g with a second crop of 1.63 g.

In the final step, a solution of 3, 1.63 g, and cyclohexanone, 50 mL, in 200 mL toluene is refluxed using a Dean-Stark trap to remove 60 mL of the solvent, and a solution of aluminum tri(isopropoxide), 2.0 g, in 20 mL dry toluene is added and the mixture refluxed for 3 hours. The reaction mixture is cooled, ether and water are added, and the ether is washed with 2% aqueous potassium hydroxide and then steam distilled. The resulting mixture is extracted with ether, and the ether is dried, decolorized with charcoal, and evaporated to give pregn-4-en-20-yn-3-one, 3.6 g, as a yellow oil. The oil is purified by chromatography on silica gel, 40 g, eluting with benzene/ethyl acetate, 99:1 and 19:1, to give pregn-4-en-20-yn-3-one, 1.58 g, as a crystalline material. Crystallization from ether/petroleum ether gives pregn-4-en-20-yn-3-one, 966 mg.

A person of ordinary skill in the art will have no difficulty, considering that skill and this disclosure (including the Krubiner et al. article mentioned above), in preparing pregn-4-en-20-yn-3-one.

Formulation and Administration

The pregn-4-en-20-yn-3-one may be administered nasally by any suitable route. Routes of administration include, but are not limited to, topical applications (e.g. of a dermal or preferably an intranasal cream or gel), nasal spray, nasal powder spray, aerosol, and the like. Pharmaceutical formulations generally will be formulations designed to administer the drug across mucosal membranes or transdermal formulations. Suitable formulations for each of these methods of administration may be found, for example, in Gennaro, ed., "Remington: The Science and Practice of Pharmacy", 20 ed., Lippincott Williams & Wilkins, Philadelphia, Pa., (2003). Typical preferred formulations will be aqueous solutions for nasal spray, and will contain pregn-4-en-20-yn-3-one and water, typically will also contain one or more other pharmaceutically acceptable excipients to increase the aqueous solubility of the pregn-4-en-20-yn-3-one, such as alcohols and glycols (for example, ethanol and propylene glycol), and may also contain one or more other pharmaceutically acceptable excipients such as preservatives, tonicifiers, and the like, such as are well-known for aqueous solutions for nasal spray. Suitable delivery devices for these formulations are the metered-dose nasal spray pumps in common use for intranasal delivery of steroids for allergies and asthma. Such pumps are made by a number of manufacturers. Liquid volumes should be such that the formulation is efficiently delivered without exceeding the nasal retention volume with an excess either flowing back into the nasal sinuses or dripping from the nose, and a volume of 50 μL has been found convenient, though greater or lesser volumes will also be satisfactory. An exemplary formulation includes the one discussed in the Detailed description of the invention under "Example 3: Human clinical studies with pregn-4-en-20-yn-3-one"; and a person of ordinary skill in the art will have no difficulty, considering that skill and this disclosure, in preparing suitable formulations and delivery systems of pregn-4-en-20-yn-3-one for nasal administration.

A therapeutically effective amount of pregn-4-en-20-yn-3-one, when administered in a nasal spray formulation of the type above, is about 400 to 4000 nanograms per administration, preferably 1000 to 2000 nanograms per administration, for example about 1600 nanograms per administration (or one-half that per nostril, assuming that the compound is administered to both nostrils). It is expected that not more than a few percent of this dose will actually reach the nasal chemosensory receptors and the VNO, so therapeutically effective amounts when administered essentially solely to the nasal chemosensory receptors will be perhaps 20-fold lower. A person of ordinary skill in the art will have no difficulty, considering that skill and this disclosure, in determining a therapeutically effective amount of pregn-4-en-20-yn-3-one for other formulations. These doses, both nasal/intranasal and direct vomeronasal/to the nasal chemosensory receptors, are well below any level that would cause a systemic effect other than those effects mediated through the nasal chemosensory receptors including receptors of the VNO.

Initial physiological response to the nasal administration of pregn-4-en-20-yn-3-one takes place very rapidly, typically within seconds to a minute after administration. Psychological response occurs more slowly; but an effect on a depressive disorder (or on one or more symptoms of the depressive disorder) is seen within 1 week, and may be expected within 1 day, for example within 4 hours, such as within 1 hour or even within 15 minutes. Because of the rapid onset of effect and safety of nasally administered pregn-4-en-20-yn-3-one, it is expected that the compound may be administered as needed, for example immediately an individual senses the onset of an episode of a symptom of the depressive disorder (such as an episode of depressed mood), to relieve and palliate the symptoms of that episode. It is also expected that the compound may be administered chronically, such as over a period of weeks or months to prevent or minimize the depressive disorder or a symptom thereof, by scheduled administration throughout the day, such as from 2 to 8 times/day, for example from 3 to 5 times/day, such as 4 times/day. This scheduled administration may be on a uniform schedule, for example at 8 a.m., noon, 4 p.m., and 8 p.m. (for 4 times/day administration), or on a non-uniform schedule where the administration is correlated with the circadian rhythm of episodes of symptoms of the depressive disorder, either in the depressive disorder symptomatic population or in the individual being treated. Thus, for example, administration might be at 9 a.m., 3 p.m., 5 p.m., and 8 p.m. (again for 4 times/day) to maximize the administration at the time when the frequency of occurrence of symptoms is greatest. Of course, even if scheduled administration is being used, it is possible to administer the compound on an as-needed basis if symptoms are still experienced.

Also, because of the rapid onset of effect of nasally administered pregn-4-en-20-yn-3-one, it is expected that the compound may be administered as an adjunct to conventional (e.g. oral) antidepressant therapy. For example, it may be administered immediately an individual is started on conventional antidepressant therapy to provide interim treatment for the period of several weeks while the conventional antidepressant becomes effective and side effects subside; it may be used as "rescue" medication in individuals who may still suffer from an episode of a symptom of the depressive disorder (such as an episode of depressed mood) even while on conventional antidepressant therapy, to relieve and palliate the symptoms of that episode as needed; or it may be used in a scheduled fashion together with conventional antidepressant therapy as a part of a complete antidepressant regimen.

Thus nasally administered pregn-4-en-20-yn-3-one may be used both acutely and chronically, and alone and in combination with conventional antidepressant therapy, in the treatment of depressive disorders.

EXAMPLES

Example 1: Electrophysiological Studies with pregn-4-en-20-yn-3-one

Pregn-4-en-20-yn-3-one induced inward currents in isolated human nasal chemosensory neurons and electrotonic depolarization of the nasal septal chemosensory epithelium: the first event in chemotransduction in peripheral receptors. The amplitude of this response increased depending on the concentration of the compound, with a maximal response at $10^{-7}$ to $10^{-5}$ M. In vitro, there was no agonist or antagonist activity on estrogen, androgen, progestin and glucocorticoid receptors, nor was there any affinity for receptors of indoleamine, monoamines, ion channels, receptors, peptides, opioid, glutamate neurotransmitter, steroid hormones, or glucocorticoid receptors, suggesting that the compound exerts its effects through specific receptors that are different from the other described binding sites.

Example 2: Preclinical Studies with pregn-4-en-20-yn-3-one

Genotoxicity tests revealed no evidence of mutagenic or clastogenic potential of pregn-4-en-20-yn-3-one when examined in the Ames reverse mutation assay and the in vivo bone marrow micronucleus test. Reproductive toxicity studies in pregnant rats and rabbits revealed no adverse effects on maternal or litter parameters attributable to the compound at intravenous doses up to 2.5 mg/Kg/day administered during the period of organogenesis.

Preclinical pharmacokinetic studies with the compound demonstrated very low systemic exposure (below the limit of accurate quantitation) when the compound was administered by repeated intranasal doses at 10 mg/Kg in the rat. Intraperitoneal administration of up to 200 mg/Kg to mice of both sexes caused no mortality or adverse symptoms during a 7-day period, and no macroscopic or microscopic changes were found in all organs studied. Intravenous administration of 1 mg/Kg to rats of both sexes produced no changes in behavior during an 8-day period, and no pathological changes were found. Intranasal and intravenous administration of up to 2.5 mg/Kg to mice, rats, rabbits and dogs caused no deaths or adverse clinical signs, no physiological changes, or changes in clinical laboratory parameters. Intranasal administration of up to 50 µg/day to rats for one month produced no deaths or adverse clinical signs or effects on laboratory or pathology parameters observed. Intranasal administration of up to 300 µg/day to dogs for 28 days produced no deaths or adverse clinical signs or effects on the laboratory or pathology parameters observed.

Example 3: Human Clinical Studies with pregn-4-en-20-yn-3-one

In pilot trials with healthy volunteers of both sexes, the nasal administration of pregn-4-en-20-yn-3-one was well tolerated and induced similar pharmacological activity in both sexes. Intranasal administration of the compound did not produce statistically significant change in heart rate and respiratory rate, and did not change the duration of the $QT_C$ intervals of the electrocardiogram. The compound did significantly increase the frequency of electrodermal activity events (measured as skin conductance), but did not have significant effect on body temperature or the alpha and beta frequency bands of an electroencephalogram.

In a Phase 1 open-label, flexible dose-escalation trial, the pregn-4-en-20-yn-3-one was formulated as an aqueous solution at 8 µg/mL, with 2% propylene glycol and 2% ethanol, and was administered with a Valois intranasal metered spray pump delivering 50 µL, so that the pregn-4-en-20-yn-3-one was administered at 400 ng/spray. The low-dose group received 400, 400, 1600, 1600, 2800, and 2800 ng/day over the six-day period of the trial, while the high-dose group received 4000, 4000, 5200, 5200, 6400, and 6400 ng/day over the six-day period of the trial. The trial enrolled 10 individuals, 7 male and 3 female, between 21 and 38 years old, healthy, free of any Axis I diagnosis according to the DSM-IV-TR, and not taking any central nervous system medications.

There were no serious adverse events; and the most frequent adverse events were increased appetite, and dizziness in the high dose group. There were no statistically significant differences in any of the safety parameters evaluated between the three doses administered to each treatment group. No statistically significant differences in clinical laboratory values, assessment of neuropsychological functioning, and evaluation of brain activity were found between the different doses of pregn-4-en-20-yn-3-one or between different visits.

In a Phase 2 three-arm, double-blind, randomized trial, individuals received either placebo (a nasal solution containing no pregn-4-en-20-yn-3-one), 3200 ng/day of pregn-4-en-20-yn-3-one ("low dose"), or 6400 ng/day of pregn-4-en-20-yn-3-one ("high dose"), formulated and administered as in the Phase 1 trial. The placebo group and the low dose group administered two sprays per nostril twice/day, the high dose group administered two sprays per nostril four times/day. The trial enrolled 30 individuals, male and female between 18 and 60 years old, meeting the diagnostic criteria for MDD and free of any other Axis I diagnosis according to the DSM-IV-TR, non-suicidal, and not taking any central nervous system medications (including natural products such as St. John's wort). The individuals were required to have a minimum score on the Hamilton Rating Scale for Depression (HRSD-17), a 17-item scale designed for completion by a health professional following a structured interview with the individual, of at least 17, meaning that they were at least moderately depressed; and the primary efficacy criterion in the trial was reduction in HRSD-17 score from baseline.

The trial included ten weekly visits. At the first (screening) visit, the individuals were assessed for depression symptoms and randomized into treatment groups. The average HRSD-17 scores for the three groups at this screening visit were: placebo, 22.3 (standard deviation 3.5); low dose pregn-4-en-20-yn-3-one, 23.9 (5.4); and high dose pregn-4-en-20-yn-3-one, 26.7 (5.9); indicating that all individuals were severely to very severely depressed. At the second (baseline) visit, they were assessed, trained in self-administration of the nasal spray, and began self-administration of their trial medication. There were seven visits at which they were assessed while on treatment with their trial medication; and one follow-up visit one week after the end of medication administration at which they were given final assessments.

All three groups showed a decrease in average HRSD-17 score from baseline during the eight weeks of treatment: placebo by 12.7 (4.7); low dose pregn-4-en-20-yn-3-one by 18.3 (7.7), with Cohen's d relative to placebo=0.86; and high dose pregn-4-en-20-yn-3-one by 18.6 (8.7), with Cohen's d relative to placebo=0.82. [Cohen's d is the mean difference between groups divided by the pooled standard deviation. For behavioral measures, a Cohen's d of 0.2 represents a small treatment effect; 0.5, a medium treatment effect; and 0.8, a large treatment effect.] There were no serious adverse events reported in any of the groups. HRSD-17 item 4 measures initial insomnia (difficulty in falling asleep early in the night), and is scored 0, for no difficulty falling asleep; 1, for complaints of occasional difficulty falling asleep, i.e. more than ½ hour; and 2, complaints of nightly difficulty falling asleep. All three groups showed a decrease in HRSD-17 item 4 from baseline during the eight weeks of treatment: placebo by 0.3 (0.15); low dose pregn-4-en-20-yn-3-one by 0.6 (0.3), with Cohen's d relative to placebo=0.39; and high dose pregn-4-en-20-yn-3-one by 1.4 (0.25), with Cohen's d relative to placebo=1.60.

These data demonstrate the safety and efficacy of the nasal administration of pregn-4-en-20-yn-3-one in the treatment of depressive disorders, and the beneficial effect of the nasal administration of pregn-4-en-20-yn-3-one on initial insomnia in depressed individuals.

While this invention has been described in conjunction with specific embodiments and examples, it will be apparent to a person of ordinary skill in the art, having regard to that skill and this disclosure, that equivalents of the specifically disclosed materials and methods will also be applicable to this invention; and such equivalents are intended to be included within the following claims.

I claim:

1. A method of treating a depressive disorder in an individual suffering therefrom, comprising nasal administration of a therapeutically effective amount of pregn-4-en-20-yn-3-one.

2. The method of claim 1, where the nasal administration includes vomeronasal administration.

3. The method of claim 1, where the individual is a man.

4. The method of claim 1, where the individual is a woman.

5. The method of claim 1, where the pregn-4-en-20-yn-3-one is administered at the onset of an episode of a symptom of the depressive disorder.

6. The method of claim 1, where the pregn-4-en-20-yn-3-one is administered chronically.

7. The method of claim 1, where the pregn-4-en-20-yn-3-one is administered on a schedule throughout the day.

8. The method of claim 7, where the pregn-4-en-20-yn-3-one is administered from 2 to 8 times per day.

9. The method of claim 8, where the pregn-4-en-20-yn-3-one is administered from 3 to 5 times per day.

10. The method of claim 9, where the pregn-4-en-20-yn-3-one is administered 4 times per day.

11. The method of claim 7, where the administration of the pregn-4-en-20-yn-3-one is on a uniform schedule.

12. The method of claim 7, where the administration of the pregn-4-en-20-yn-3-one is on a non-uniform schedule to maximize the administration at the time when the frequency of occurrence of symptoms of the depressive disorder is greatest.

13. The method of claim 1, where a treatment effect on the depressive disorder, or on at least one symptom of the depressive disorder, is seen within 1 week of the administration of the pregn-4-en-20-yn-3-one.

14. The method of claim 1, where the individual is also administered conventional antidepressant therapy.

15. The method of claim 1, where the pregn-4-en-20-yn-3-one is administered in a pharmaceutical formulation.

16. The method of claim 15, where the pharmaceutical formulation is a nasal spray.

17. The method of claim 16, where the nasal spray comprises an aqueous solution of pregn-4-en-20-yn-3-one.

18. The method of claim 17, where the nasal spray comprises 8 µg/mL pregn-4-en-20-yn-3-one, 2% propylene glycol, and 2% ethanol.

19. The method of claim 16, where the pregn-4-en-20-yn-3-one content of the nasal spray is 400 to 4000 nanograms per administration.

20. The method of claim 1, where the individual suffering from a depressive disorder is also suffering from insomnia.

21. The method of claim 1, where the depressive disorder is Major Depressive Disorder.

* * * * *